United States Patent
Voges et al.

(10) Patent No.: US 10,938,415 B2
(45) Date of Patent: Mar. 2, 2021

(54) METHOD FOR ENCODING AND DECODING OF QUALITY VALUES OF A DATA STRUCTURE

(71) Applicant: GOTTFRIED WILHELM LEIBNIZ UNIVERSITÄT HANNOVER, Hannover (DE)

(72) Inventors: Jan Voges, Hannover (DE); Jörn Ostermann, Hannover (DE)

(73) Assignee: GOTTFRIED WILHELM LEIBNIZ UNIVERSITÄT HANNOVER, Hannover (DE)

( * ) Notice: Subject to any disclaimer, the term of this patent is extended or adjusted under 35 U.S.C. 154(b) by 0 days.

(21) Appl. No.: 16/630,891

(22) PCT Filed: Jul. 16, 2018

(86) PCT No.: PCT/EP2018/069231
§ 371 (c)(1),
(2) Date: Jan. 14, 2020

(87) PCT Pub. No.: WO2019/012153
PCT Pub. Date: Jan. 17, 2019

(65) Prior Publication Data
US 2020/0153454 A1    May 14, 2020

Related U.S. Application Data

(60) Provisional application No. 62/532,381, filed on Jul. 14, 2017.

(51) Int. Cl.
*H03M 7/30*    (2006.01)
*G16B 30/10*   (2019.01)
(Continued)

(52) U.S. Cl.
CPC ............ *H03M 7/70* (2013.01); *G16B 30/10* (2019.02); *G16B 50/00* (2019.02);
(Continued)

(58) Field of Classification Search
CPC .......... G06F 19/22; G06F 19/18; G06F 19/24; G06F 19/28; G06F 19/00; H03M 7/40; H03M 7/30
(Continued)

(56) References Cited

U.S. PATENT DOCUMENTS

2016/0306922 A1* 10/2016 van Rooyen ....... G06F 19/3418

OTHER PUBLICATIONS

Marpe et al: "Context-Based Adaptive Binary Arithmetic Coding in the H.264/AVC Video Compression Standard", IEEE Transactions on Circuits and Systems for Video Technology, vol. x, No. y, 2003.
(Continued)

*Primary Examiner* — Joseph J Lauture
(74) *Attorney, Agent, or Firm* — W&C IP

(57) ABSTRACT

Method for encoding of quality values of a data structure, whereby said data structure comprises a set of genomic reads, wherein the method comprises the following steps executable by a data processing system: ascertain the quality values of each read covering a certain index locus, —determine a codebook identifier identifying a specific codebook from a plurality of codebooks for said certain index locus based on the ascertained quality values of said certain index locus, whereby each code-book provides a mapping from a quality value of said quality value alphabet to a corresponding quantized quality value of a quantized quality value alphabet, —quantizing all ascertained quality values at said certain index locus using the specific codebook identified by the codebook identifier at said certain index locus in order to obtain for each quality value at said certain index locus a corresponding quantized quality value, and —encode all
(Continued)

determined codebook identifiers using a first entropy encoder and encode all quantized quality values using a second entropy encoder or a set of encoders.

12 Claims, 2 Drawing Sheets

(51) Int. Cl.
 *G16B 50/00* (2019.01)
 *H03M 7/40* (2006.01)
(52) U.S. Cl.
 CPC ............ *H03M 7/4006* (2013.01); *H03M 7/30* (2013.01); *H03M 7/40* (2013.01)
(58) Field of Classification Search
 USPC .................................................... 702/20, 19
 See application file for complete search history.

(56) References Cited

OTHER PUBLICATIONS

Li et al: "The Sequence Alignment/Map format and SAMtools", Bioinformatics, vol. 25, No. 16, pp. 2078-2079, 2009.
"Text of ISO/IEC 23092-2 WD 2, Coding of Genomic Information" ISO/IEC JTC 1/SC 29/WG, ISO/TC 276/WG 5, Feb. 15, 2017.
"Core Experiments on Genomic Information Representation", ISO/IEC JTC1/SC29/WG11, Apr. 2017.

* cited by examiner

METHOD FOR ENCODING AND DECODING OF QUALITY VALUES OF A DATA STRUCTURE

FIELD OF THE INVENTION

The present invention relates to a method and to a corresponding device for encoding of quality values of a data structure, especially of genomic data stored as such data structure. The present invention relates also to a method for decoding of quality values of data structure, which was encoded by a method of the present invention.

BACKGROUND

Due to novel high-throughput sequencing (HTS) and or next-generation sequencing (NGS) technologies, the sequencing of huge amounts of genetic information has become affordable. Because of this float of data, IT costs may count a major obstacle compared to sequencing costs. High-performance compression of genomic data is required to reduce the storage size and the transmission costs.

Sequencing machines produced a multitude of readouts (in short: reads) of fragments of nucleotide sequences. During the sequencing process, quality values, also known as quality scores, are assigned to each nucleotide in a nucleotide sequence of a readout. This quality values express the confidence that the corresponding nucleotide has been read out correctly or not.

In Peter J A Cock, Christopher J Fields, Naohisa Goto, Michael L Heuer, and Peter M Rice. The Sanger FASTQ_le format for sequences with quality scores, and the Solexa/Illumina FASTQ variants. Nucleic Acids Research, 38(6):1767{1771, 2010, is a FASTQ file format for sequences with quality scores disclosed. After the raw data has been generated, some of the most common subsequent processing steps are:

a) Reference-based alignment of the reads with tools such BWA (Heng Li and Richard Durbin. Fast and accurate short read alignment with Burrows-Wheeler transform. Bioinformatics, 25(14):1754{60, 2009), Bowtie (Ben Langmead and Steven L. Salzberg. Fast gapped-read alignment with Bowtie 2. Nature Methods, 9(4):357{9, 2012, Ben Langmead, Cole Trapnell, Mihai Pop, and Steven L. Salzberg. Ultrafast and memory-e_cient alignment of short DNA sequences to the human genome. Genome Biology, 10(3):R25.1{10, 2009), mrsFAST (Faraz Hach, Fereydoun Hormozdiari, Can Alkan, Farhad Hormozdiari, Inan_c Birol, Evan E Eichler, and S Cenk Sahinalp. mrsFAST: a cache-oblivious algorithm for short-read mapping. Nature Methods, 7(8):576-7, August 2010) or GEM (Santiago Marco-Sola, Michael Sammeth, Roderic Guig_o, and Paolo Ribeca. The GEM mapper: fast, accurate and versatile alignment by _ltration. Nature Methods, 9(12):1185{1188, October 2012) or b) De-novo assembly of the reads with tools such ABySS (Jared T Simpson, Kim Wong, Shaun D Jackman, Jacqueline E Schein, Steven J M Jones, and Inan_c Birol. ABySS: a parallel assembler for short read sequence data. Genome Research, 19(6):1117{23, June 2009) or SPAdes (Anton Bankevich, Sergey Nurk, Dmitry Antipov, Alexey A Gurevich, Mikhail Dvorkin, Alexander S Kulikov, Valery M Lesin, Sergey I Nikolenko, Son Pham, Andrey D Prjibelski, Alexey V Pyshkin, Alexander V Sirotkin, Nikolay Vyahhi, Glenn Tesler, Max A Alekseyev, and Pavel A Pevzner. SPAdes: A New Genome Assembly Algorithm and Its Applications to Single-Cell Sequencing. Journal of Computational Biology, 19(5):455-77, May 2012).

During the alignment or assembly process, additional information is generated for each read, such as the mapping positions or the CIGAR strings. The latter express of different operations needed to be performed on a read so that it maps perfectly to the reference sequence used for alignment or assembly. The reads are extended with this additional information to form so-called alignments, which can e.g. be stored in the SAM format (Heng Li, Bob Handsaker, Alec Wysoker, Tim Fennell, Jue Ruan, Nils Homer, Gabor Marth, Goncalo Abecasis, and Richard Durbin. The Sequence Alignment/Map format and SAMtools. Bioinformatics, 25(16):2078{2079, 2009; Jan Voges, Marco Munderloh, and Jorn Ostermann. Predictive Coding of Aligned Next-Generation Sequencing Data. In Data Compression Conference (DCC), pages 241{250, Snowbird, UT (US), 2016. IEEE).

In WO 2018/068845 A1 is a method for encoding and decoding of quality values of a data structure disclosed. An estimation certainty at a specific locus index is calculated based on the quality values and each quality value is transformed into a transformed quality value based on the calculated estimation certainty.

SUMMARY

It is an aspect of the present invention to provide a better encoding and compression method for compressing quality values of a genomic data structure which was sequenced. It is a further aspect of the present invention to provide a decoding or decompression method for decoding such encoded quality values of genomic data.

According to claim 1 a method for encoding of quality values of a genomic structure posed. The genomic data structure comprises a plurality of genomic reads, whereby each genomic read was obtained by a sequencing process of a donor sequence or donor genome.

Based on the specification of such genomic data structures, each read includes an actual sequenced nucleotide sequence, which could be a fragment or a local part of said donor genome. Each genomic read includes further a mapping position, a CIGAR string and a sequence of quality values to be encoded. The actual sequenced nucleotide sequence of one read includes a sequence of symbols derived from a nucleotide alphabet. In the most cases sequencing DNA or RNA, a nucleotide alphabet includes C, T, A, G and/or U.

The addressed mapping position indicating, further, an alignment of said nucleotide sequence relating to at least one reference nucleotide sequence of the donor genome. A CIGAR string indicating similarities and/or differences of said nucleotide sequence relating to at least one of said referenced nucleotide sequence and the quality values indicating a likelihood that the corresponding symbol of the nucleotide sequence is correct in view of at least one of said referenced nucleotide sequence.

For example, such data structure could be saved in a data file, for example a SAM file.

The method for encoding such quality values to reduce the information density for reducing the memory space of the data structure comprises the following steps executable by a data processing system. At first, at a certain index locus, the quality values of each read covering said certain index locus is ascertained. After this step, at a specific locus index, each possible quality value with the same index locus are known from the data structure.

In the next step, a codebook identifier is determined based on the ascertained quality values of a certain index locus. This codebook identifier identifies a specific codebook from a plurality of codebooks for said certain index locus, whereby each codebook provides a mapping from a quality value of said quality value alphabet to a corresponding quantized quality value of a quantized quality value alphabet. To reduce the information density for reducing the memory space, the cardinality of the quantized quality value alphabet is much smaller than the cardinality of the quality value alphabet.

Based on such mapping in the codebooks, different quality values can be mapped to the same quantized quality value.

After ascertaining the quality values at the certain index locus and determining the specific codebook for said certain index locus, all ascertained quality values are quantized using the specific codebook identified by the codebook identifier in order to obtain for each quality value at said certain index locus a corresponding quantized quality value.

If all quality values at one or more certain index locus are quantized, all determined codebook identifiers are encoded using a first entropy encoder and all quantized quality values are encoded using a second entropy encoder or a set of second entropy encoders. Such encoders could be arithmetic encoders.

This invention makes it possible to reduce the memory space for the quality values in such a way that quality values at a certain index locus relating to good sequence nucleotides has a better or higher compression rate than quality values relating to poor sequence nucleotides. That is, if the method believes that two or more different genotypes or nucleotides are likely to be true, the method will yield less compressibility at that locus index. However, if there is enough evidence in the data that a particular genotype is likely the correct one, the method will yield more compression.

Advantageously, the quantization steps are performed for each index locus possible in the genomic data structure.

In an embodiment, a genotype uncertainty for a set certain index locus is computed based on the ascertained quality values at that certain index locus and the corresponding nucleotide symbols to which the ascertained quality values belong. For computing said genotype uncertainty, a statistical model is used in order to obtain a likeliness that a unique genotype is the correct one.

In a further embodiment, the determined codebook identifier at said certain index locus is inputted into a quality value codebook stream and the quantized quality values at said certain index locus are inputted into a quality value index stream or a set of quality values index streams. This is performed after the ascertained quality values are quantized using the codebook identified by the codebook identifier and before the codebook identifiers and the quantized quality values are encoded. Subsequently, if all necessary quality values at one or more index loci are quantized and inputted into the quality value index stream as well as the codebook identifiers inputted into the quality value codebook stream. The codebook identifiers of the quality value codebook streams are encoded using the first entropy encoder and the quantized quality values of the quality value index stream are encoded using the second entropy encoder or a set of second entropy encoders. The entropy encoders can be arithmetic encoders.

Each index of the quality value codebook stream relates to an index locus and relates to an index of the quality value index stream corresponding to quantized quality values at this index locus.

In a further embodiment, the quality value index stream is decomposed into (disjunkt) subsequence streams corresponding to the provided codebook identifiers such that each subsequence stream is assigned to one codebook identifier of the codebook identifiers. In other words, for each codebook identifier identifying a special codebook exists one subsequence stream of a quality value index stream, whereby all quality values which were quantized by the same codebook are inputted into a subsequence stream which is assigned to a codebook identifier identifying this special codebook. The term decomposed means that the quality value index stream is demultiplexed into such subsequence streams, whereby the demultiplexing process uses the codebook identifiers to indicate each demultiplexed subsequence stream.

Then, each subsequence stream is separately encoded using the second entropy encoder or a set of second entropy encoders, so that all quality values quantized using the same codebook are encoded by the same entropy encoder.

In a further embodiment thereto, for each subsequence stream a probability distribution is computed based on the quality values of the respective subsequence stream and a separate second entropy encoder modelling the probability distribution of the respective subsequence stream is used for encoding the respective subsequence stream.

According to claim 7, a method for decoding of encoded quality values are proposed, whereby the encoded quality values were encoded by a method mentioned above. The method comprises the following steps executable by a data processing system:

decode the encoded codebook identifiers and the encoded quantized quality values using an entropy decoder corresponding to the entropy encoders of the encoding method;

ascertain a codebook identifier for a certain index locus from the decoded codebook identifiers and quantized quality values for said certain index locus from the decoded quantized quality values;

determine a specific codebook of the plurality of codebooks based on the ascertained codebook identifier, and reconstruct the ascertained quantized quality values using the determined specific codebook.

In an embodiment, the steps are performed for each index locus.

BRIEF DESCRIPTION OF THE DRAWINGS

The present invention is described in more detail by reference to the following figures.

DETAILED DESCRIPTION

Figure 1:
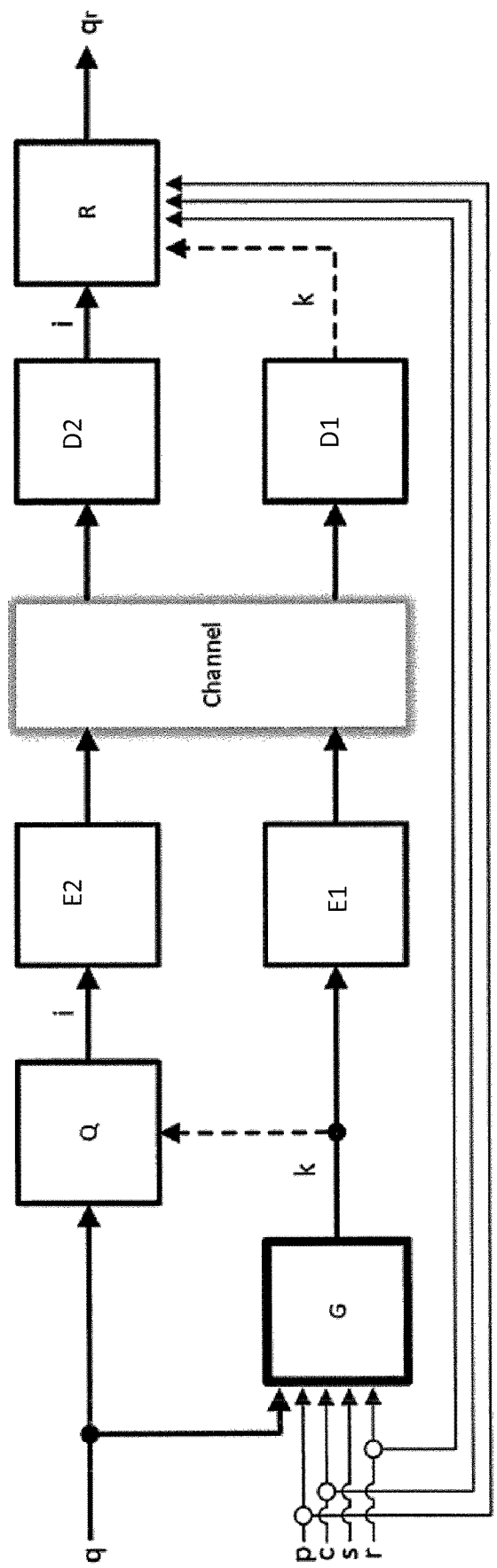
FIG. 1—overview of the coding structure.

FIG. 1 shows the basic coding structure for encoding and decoding. The encoder gets as input quality values q, mapping positions p, CIGAR strings c, nucleotide sequences s and optionally the reference sequence(s) r, as defined e.g. in the SAM format specification. The computation of the codebook identifiers k is performed by module G which gets as input the quality values q, the mapping positions p, the mapping positions p, the CIGAR strings c, the nucleotide sequences s and optionally the reference sequence(s) r. The codebook identifiers k then control the working of the quantization module Q which quantized the quality values q and outputs quantized quality values i.

The codebook identifier k is used to quantize all quality values associate with index locus l, whereas a high codebook identifier k is associate with the codebook comprising a high number of representative values. In other words, a high codebook identifier k will yield fine quantization and vice versa.

To compute the codebook identifier k the proposed method infers the genotype uncertainty at locus l from the observable data using a statistical model. Given the sequencing depth N at locus l, the immediate observable data are the read-out nucleotides and the associated quality values of all reads overlapping locus l considering the information in the CIGAR strings. The genotype uncertainty can be regarded as a metric M that measures the likeliness that a unique genotype is the correct one.

More specifically, assume a set of reads that are aligned to a reference sequence or that were aligned by a de-novo assembler. Further assume that the reads were sorted by their mapping positions. Given such set of reads, let denote by N the number of reads covering locus l. Let $n_j$ be the symbol from read j covering the locus l and $q_j$ the value of the corresponding quality value. The observable data at locus l can be written as $(n, q) = \{(n_j, q_j)\}_{j=1}^N$.

For each locus l, a metric $M=M(n, q)$ (the genotype uncertainty) can be computed. Then, the codebook identifier k is computed by using the metric M as $$k = f(M(n,q)),$$

where f is a monotonous increasing function.

That is, if the method believes that two or more different genotypes are likely to be true, than the genotype uncertainty will be high and hence, k will be high, which will yield less compressibility at the locus l. However, if there is enough evidence in the data that a particular genotype is likely the correct one, than the genotype uncertainty will be low, and therefore, k will be low, which will yield more compression.

The quantization index i and the codebook identifier k are encoded by entropy encoder module E1 and E2. The quantization index i are encoded by entropy encoder module E2, while the codebook identifiers k are encoded by entropy encoder module E1.

After transmission over the transmission channel, the decoder decodes the quantization indexes using entropy decoder module D2 and decodes the codebook identifiers using entropy decoder module D1. The alignment information, i.e. the mapping positions, the CIGAR strings, and the reference sequence must be transmitted as side information to the decoder. Subsequently, using the quantization indexes, the codebook identifiers and the side information, the reconstruction module r reconstructs the quality values.

The quantized quality values (mentioned above as quantization indexes i) are inputted into a quality value index stream. The codebook identifiers k are inputted into a quality value codebook stream. In a single-stream entropy encoding stream, the quality value codebook stream and the quality value index streams are compressed block wise with two arithmetic encoders. Here, in an example, the first arithmetic encoder modules the probability distribution P(k) for the quality value codebook stream symbols $K=\{0, \ldots, k\}$ therefore approaching the memoryless entropy of the quality value codebook stream signal. The second arithmetic encoder models the probability distribution P(i) for the symbols of the quantized quality value alphabet l, therefore approaching the memoryless entropy of the quality value index stream signal.

Figure 2:
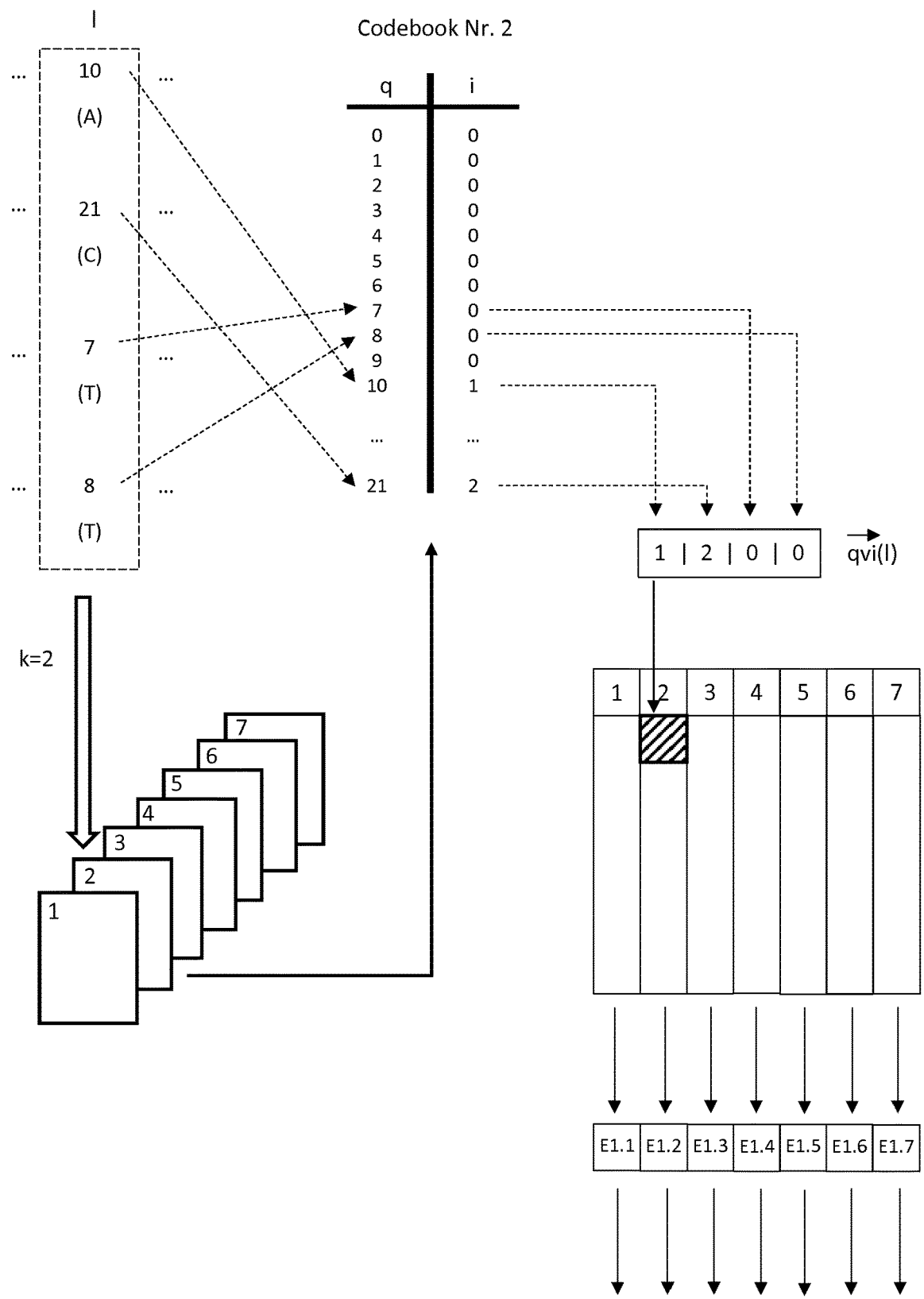
FIG. 2—detailed description of the encoding method using a simple example.

In a context-based entropy encoding stream, as shown in a simple example in FIG. 2, the quality value index stream is decomposed respectively demultiplexed into (disjunkt or disjoint) subsequence streams corresponding to the number of codebooks K. For example, the number of codebooks could be 7, so that the quality value index stream is decomposed into subsequence streams corresponding to the codebook identifier symbols k element $\{1, 2, 3, 4, 5, 6, 7\}$. The codebook identifier symbol 0 is sent at loci with 0 sequencing depth.

The example in FIG. 2 shows four reads at the specific locus l, whereby the first read at locus l had a nucleotide A, the second read a nucleotide C, the third read a nucleotide T and the last read the nucleotide T. The quality value at locus l for the first read has a value of 10, the second value of 21, the third value of 7 and the last value of 8.

Based on the quality values 10, 21, 7, 8 at the specific locus l and the nucleotides A, C, T, T, the codebook identifier k is computed. Based on the codebook identifier k, a codebook from a plurality of codebooks is determined, whereby the determined codebook relating to the codebook identifier k. In the example of FIG. 2, k=2 and the codebook with the number 2 is chosen. This codebook has the quantization indexes or quantized quality values $I=\{0, 1, 2\}$. Based on the chosen codebook number 2 and the quality values $\{10, 21, 7, 8\}$ at locus l, the quantized quality values i are computed using the codebook number 2. Therefore, for the quality value 10 a quantized quality value 1 is determined. For the quality value 21, a quantized quality value 2 is used. For the quality value 7 and 8, the quantized quality value of 0 is determined from the codebook number 2.

Furthermore, seven (disjunkt or disjoint) quality value index streams (known as subsequence streams) are exist. In the subsequence streams corresponding to the codebook number 2, the quantized quality values $\{1, 2, 0, 0\}$ at locus l are inputted.

Quantized quality values quantized by another codebook are inputted into the stream relating to the corresponding codebook. Hence, the quantized quality values i are grouped into seven subsequence streams which than are separately compressed by seven arithmetic encoders which model the probability distributions ($p(i|k_i)$).

Every codebook identifier k is associated to a specific genomic locus l. Also, every quantized quality value symbol i is associate to a specific genomic locus. Given a codebook identifier $k(l)=k_l$ at locus l, the possible values for all quantized quality value symbol at this locus l are also determined by $i(l)=i(k_l)$ element $\{0, \ldots, k_l\}$.

In this current implementation, seven arithmetic encoders are used which each model a different conditional probability distribution. However, other entropy encoder architectures might as well be used to exploit the statistic of the quantized quality values and codebook identifiers streams.

The invention claimed is:
1. A method for encoding of quality values of a data structure, whereby said data structure comprises a set of genomic reads, whereby each genomic read in said set of genomic reads comprises
   an actual sequenced nucleotide sequence as a local part of
      a donor sequence or genome, wherein said nucleotide
      sequence includes a sequence of symbols derived from
      a nucleotide alphabet, a mapping position indicating an alignment of said nucleotide sequence relating to at least one reference nucleotide sequence of the donor sequence or genome,
a CIGAR string indicating similarities and/or differences of said nucleotide sequence relating to said at least one reference nucleotide sequence of the donor sequence or genome, and
a sequence of quality values, each quality value being derived from a quality value alphabet, whereby a quality value at an index locus of said sequence of quality values is assigned to a corresponding symbol of said nucleotide sequence at said index locus and indicates a likelihood that the corresponding symbol is correct in view of said at least one reference nucleotide sequence of the donor sequence or genome,
wherein the method is executed by a computer including a storage medium having stored thereon processor-executable instructions to cause the computer to perform the following operations:
ascertain the quality values of each genomic read covering a certain index locus,
determine a codebook identifier identifying a specific codebook from a plurality of codebooks for said certain index locus based on the ascertained quality values of said certain index locus, whereby each codebook provides a mapping from a quality value of said quality value alphabet to a corresponding quantized quality value of a quantized quality value alphabet,
quantize all ascertained quality values at said certain index locus using the specific codebook identified by the codebook identifier at said certain index locus in order to obtain for each quality value at said certain index locus a corresponding quantized quality value, and
encode all determined codebook identifiers using a first entropy encoder and encode all quantized quality values using a second entropy encoder or a set of encoders,
wherein the encoded codebook identifiers and the encoded quantized quality values are stored in a memory space in place of storing the quality values or the actual sequenced nucleotide sequence.

2. The method according to claim 1, wherein the quantization step is performed for each index locus.

3. The method according to claim 1, wherein a genotype uncertainty for said certain index locus is computed based on the ascertained quality values at said certain index locus and the corresponding nucleotide symbols of each quality value at said certain index locus are obtained using a statistical model in order to obtain a likeliness that a unique genotype is the correct one.

4. The method according to claim 1, further comprising the following steps executed by the data processing system:
input the determined codebook identifier at said certain index locus into a quality value codebook stream and input the quantized quality values at said certain index locus into a quality value index stream or a set of streams;
encode the codebook identifiers of the quality value codebook stream using the first entropy encoder and encode the quantized quality values of the quality value index stream using the second entropy encoder or a set of encoders.

5. The method according to claim 4 further comprising the following steps executed on the data processing system:
decompose the quality value descriptor stream into subsequence streams corresponding to the provided codebook identifiers such that each subsequence stream is assigned to one codebook identifier of the codebook identifiers,
input the quantized quality values into that subsequence stream which corresponds to the respective codebook identifier, and
encode each subsequence stream separately using the second entropy encoder or set of encoders.

6. The method according to claim 5, wherein for each subsequence stream, a probability distribution is computed based on the quality values of the respective subsequence stream and a separate second entropy encoder modelling the probability distribution of the respective subsequence stream is used for encoding the respective subsequence stream.

7. A method for decoding of encoded quality values, whereby the encoded quality values were encoded by a method according to claim 1, wherein the method is executed by a computer including a storage medium having stored thereon processor-executable instructions to cause the computer to perform the following operations:
decode the encoded codebook identifiers and the encoded quantized quality values using an entropy decoder corresponding to the entropy encoders of the encoding method;
ascertain a codebook identifier for a certain index locus from the decoded codebook identifiers and quantized quality values for said certain index locus from the decoded quantized quality values;
determine a specific codebook of the plurality of codebooks based on the ascertained codebook identifier; and
reconstruct the ascertained quantized quality values using the determined specific codebook.

8. The method according to claim 7, wherein the steps are performed for each index locus.

9. A computer program encoded on a non-transient computer readable medium having instructions which are executable on a data processing system for executing a decoding method according to claim 7.

10. A hardware device arranged to execute the decoding method according to claim 7.

11. A computer program encoded on a non-transient computer readable medium having instructions which are executable on a data processing system for executing a method according to claim 1.

12. A hardware device arranged to execute the encoding method according to claim 1.

* * * * *